United States Patent [19]

Agdanowski

[11] 4,330,497

[45] May 18, 1982

[54] METHOD OF MAKING GROOVED PLASTIC MEDICAL TUBING

[75] Inventor: Ronald T. Agdanowski, St. Peters, Mo.

[73] Assignee: Sherwood Medical Industries Inc., St. Louis, Mo.

[21] Appl. No.: 226,297

[22] Filed: Jan. 19, 1981

[51] Int. Cl.³ .............................................. B29C 17/14
[52] U.S. Cl. ................................... 264/150; 128/276; 128/350 R; 264/139; 264/154; 264/173
[58] Field of Search .............. 264/139, 150, 154, 171, 264/173; 128/276, 350

[56] References Cited

U.S. PATENT DOCUMENTS

| | | | |
|---|---|---|---|
| 2,568,566 | 9/1951 | Sokolik | 128/240 |
| 2,711,740 | 6/1955 | Pickens | 128/349 |
| 2,857,915 | 10/1958 | Sheridan | 128/349 |
| 2,940,126 | 6/1960 | Sheridan | 18/55 |
| 3,136,316 | 6/1964 | Beall | 128/350 |
| 3,752,617 | 8/1973 | Burlis | 425/131 |
| 3,848,604 | 11/1974 | Sackner | 128/350 |
| 3,921,856 | 11/1975 | Langecker | 222/132 |
| 3,945,385 | 3/1976 | Sackner | 128/350 |
| 4,138,457 | 2/1979 | Rudd et al. | 264/173 |
| 4,182,582 | 1/1980 | Youval et al. | 264/173 |
| 4,277,432 | 7/1981 | Woinowski | 264/173 |

Primary Examiner—Donald E. Czaja
Assistant Examiner—W. Thompson
Attorney, Agent, or Firm—Stanley N. Garber; William R. O'Meara

[57] ABSTRACT

Grooved tubing having a groove in the outer sidewall and a hole through the bottom of the groove is made by extruding a first plastic to produce a molten tubular extrudate, extruding a second plastic in the exterior of the sidewall of the tubular extrudate, subsequently removing the second plastic to provide a groove in the tubular extrudate and forming an opening through the bottom of the groove. This method can be used in making suction catheters wherein the groove walls prevent invagination of body tissue into the hole in the groove during suctioning.

26 Claims, 12 Drawing Figures

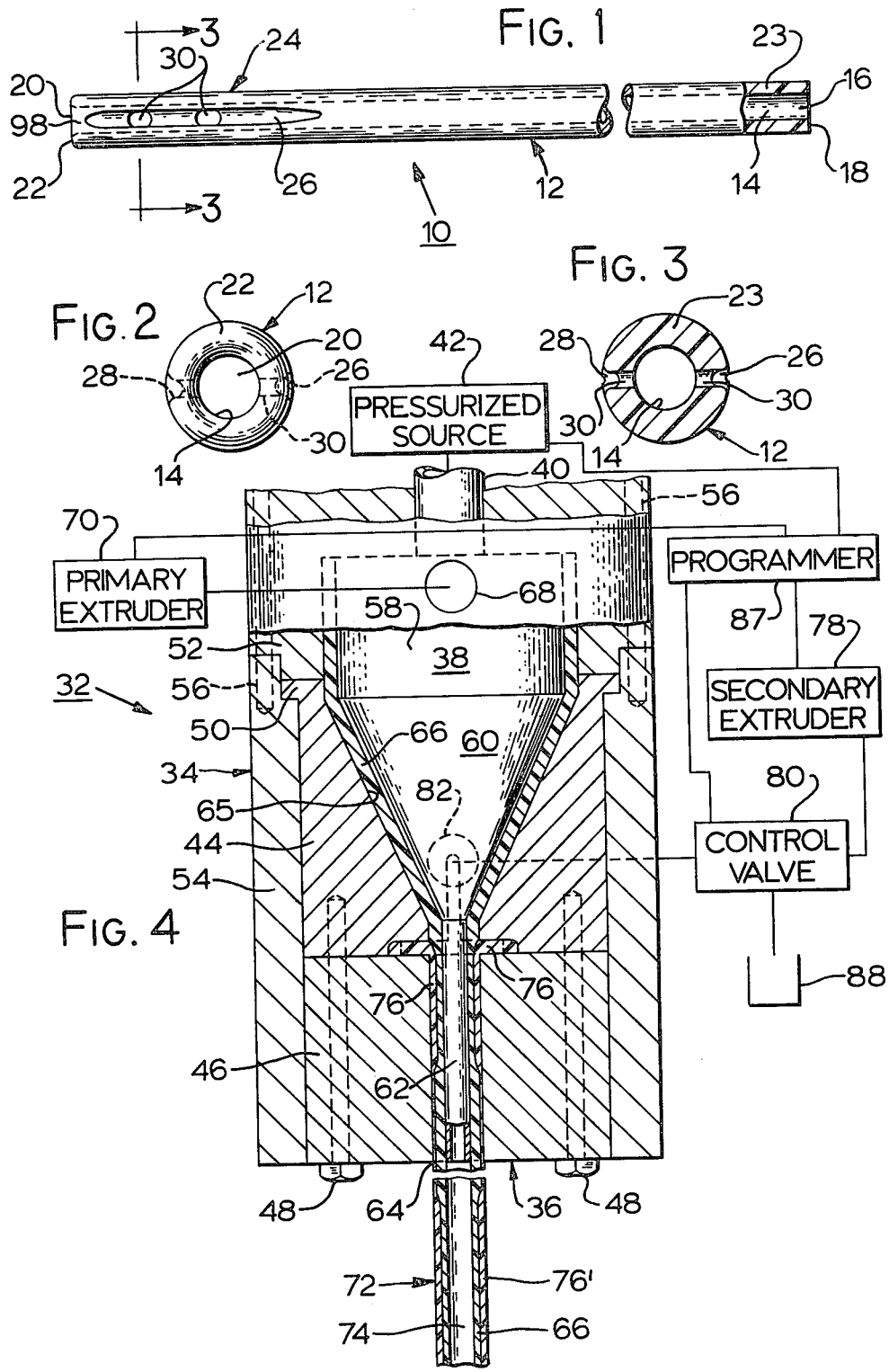

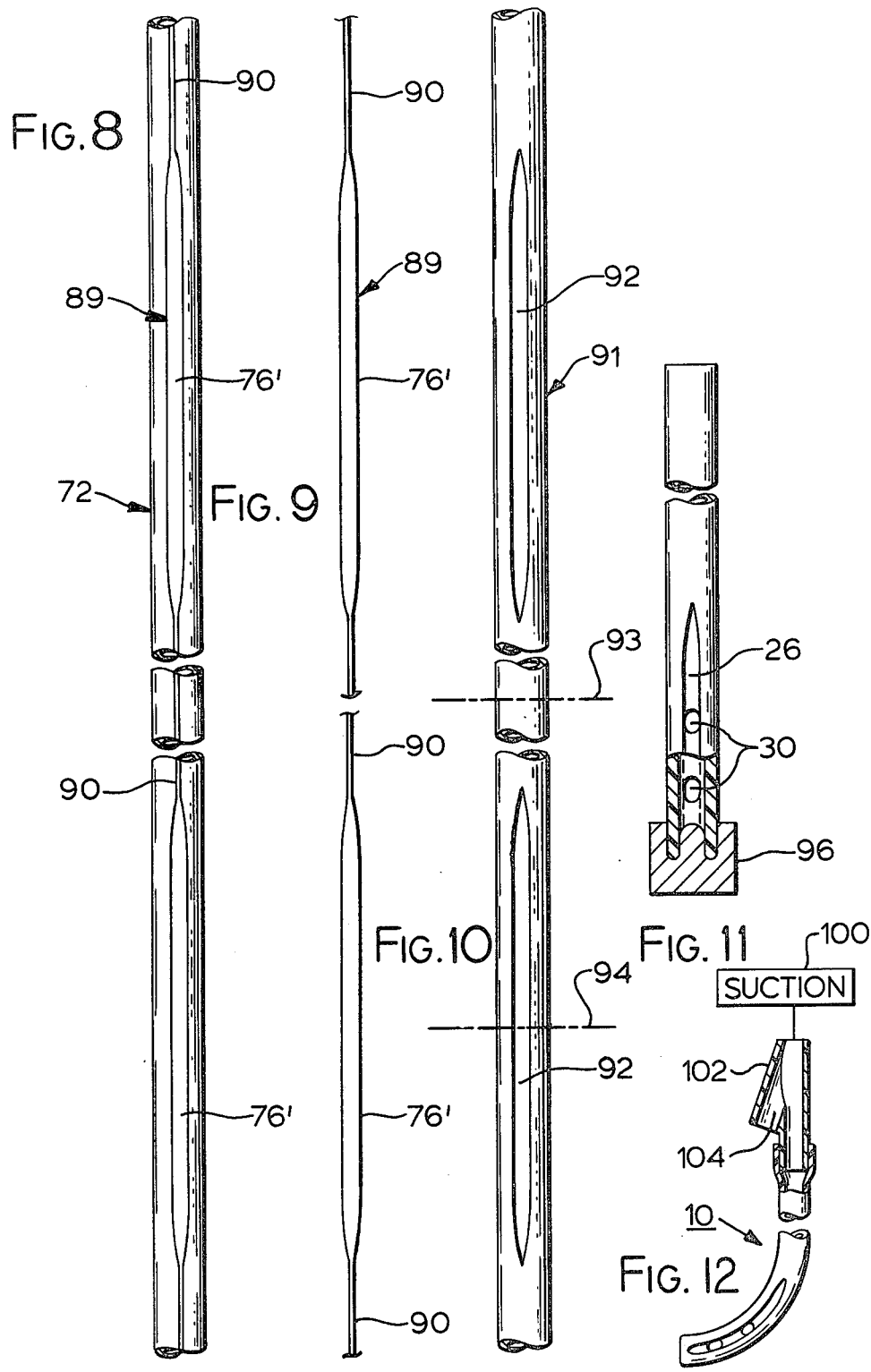

METHOD OF MAKING GROOVED PLASTIC MEDICAL TUBING

DESCRIPTION

1. Technical Field

This invention relates to a method of making plastic tubing and more particularly to a method making grooved extruded plastic tubing.

2. Background Art

Plastic tubing such as used in making suction catheters is generally extruded and then post-formed to provide a desired shape. Suction catheters are generally provided with suction openings in the sidewall adjacent the distal end of the catheter. Such suction catheters are used in a variety of applications, for example, they are used for tracheobronchial and nasopharyngeal suctioning. It is important to construct the catheter so that invagination of the mucosa or body cavity wall tissue into the suction openings is prevented so as to avoid occlusion of the openings and damage to the patient.

In some cases, an extruded thermoplastic catheter is post-formed by inserting the distal end into a mold or die and heat forming it to provide a flange, such as disclosed in U.S. Pat. No. 3,848,604, or circumferentially alternating, axially extending flanges and valleys, for example, as shown in U.S. Pat. No. 3,945,385. The suction holes are generally punched or drilled between the flanges or within the valleys or grooves. The flanges space the holes from the cavity walls to prevent invagination of the cavity wall during suctioning. However, these flanges and valleys result in either an increase in the outer diameter or a decrease in the lumen of the catheter. Where an enlargement is heat formed or attached at the distal end, the catheter must be designed with a smaller inner diameter than would be necessary for a given size body cavity if no enlargement was employed. Where the catheter is post-formed so as to have a reduction of the lumen at the distal end, the reduction generally produces a flow restriction. In other words, such post-forming of plain plastic tubes to form flanges and valleys generally reduces the flow rate efficiency of the catheter.

DISCLOSURE OF THE INVENTION

The present invention is directed to overcoming one or more of the problems set forth above and has for its object to provide an improved method of making an extruded grooved tube provided with an opening in the sidewall of the tube at the bottom of the groove.

In accordance with one aspect of the present invention, a method of making a grooved plastic tube is disclosed which includes coextruding an auxiliary plastic material with plastic tubing. The auxiliary plastic material is different from that of the tubing and is subsequently removed from the tubing thereby leaving a groove in the tubing. An opening is formed within the groove of the tubing which connects with the lumen of the tubing.

These, as well as other objects and advantages of the present invention, will become apparent from the following detailed description and accompanying drawings.

BRIEF DESCRIPTION OF THE DRAWINGS

FIG. 1 is a side view of a suction catheter made in accordance with a preferred method of the present invention;

FIG. 2 is an enlarged left end view of the catheter of FIG. 1;

FIG. 3 is an enlarged cross-sectional view taken along line 3—3, of FIG. 1;

FIG. 4 is a somewhat schematic illustration including die portions in cross-section of an extruding device used in making grooves tubing in accordance with the present invention;

FIG. 8 is an elevational view of the extrudate emanating from the die of FIG. 4;

FIG. 9 is an elevational view of auxiliary plastic strip material after being removed from the tubing extrudate illustrated in FIG. 8;

FIG. 10 is an elevational view of the tubing of FIG. 8 after the auxiliary plastic strip of FIG. 9 has been removed;

FIG. 11 is an elevational view partly in section of a portion of the tubing of FIG. 10 with one end being heat formed to provide a smooth distal end on the tubing section; and FIG. 12 is a plan view, on a reduced scale, showing the suction catheter of FIG. 1 connected to a suction source through a vacuum control device connected to the catheter.

BEST MODE FOR CARRYING OUT THE INVENTION

Figure 6:
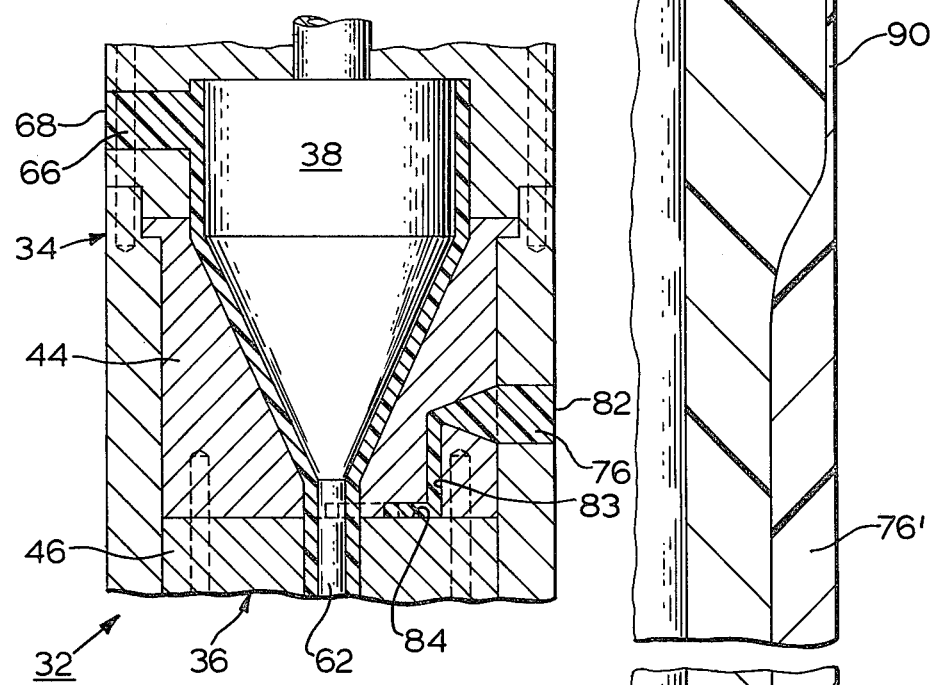
FIG. 6 is a cross-sectional view of the die shown in FIG. 4 but rotated 90° about the vertical axis of the die.

Referring now to the drawings and more particularly to FIGS. 1–3, there is shown for illustration, a medical suction catheter 10 made in accordance with the present invention and which can be used for suctioning drainage matter from a body cavity of a patient. For example, catheter 10 can be used for tracheobronchial suctioning and be made from polyvinyl chloride.

Catheter 10 has a plastic tubular body 12 with a lumen 14 extending entirely through the body so that the catheter has an axial end opening 16 at the proximal end 18 of the body, and an opening 20 at the distal end 22. Lumen 14 has a constant diameter throughout its length and the body 12 is shown having a sidewall 23 of constant thickness, thus the inner and outer diameters of the body 12 are substantially constant throughout the length of the body.

The catheter 10 has a distal end portion indicated generally at 24, that is provided with a pair of similar longitudinally extending grooves 26 and 28 in the outer or exterior surface of the sidewall 23 of the body 12, and a plurality of suction openings or holes 30 formed in the bottom wall of each of the grooves 26 and 28. Two axially spaced suction holes 30 in each of the grooves are shown extending through the sidewall 23 of the body 12 and communicating with the lumen 14. Additional grooves, like grooves 26 and 28, and additional suction holes 30 provided in the bottom walls of the grooves may be provided at the distal end 24 if desired. The sidewalls of the grooves maintain the suction holes spaced from the walls of the body cavity into which the catheter 10 is to be inserted and prevent occlusion of the holes. The distal end 22 of the catheter is shown rounded to facilitate movement of the catheter into a body cavity and reduce the chances of damage to the walls of the cavity during insertion.

The body 12 may be made of various extrudable plastic materials and is made preferably of one that is substantially nontoxic to the human body in the case of medical catheters. Depending upon its intended use, it may be made of a relatively stiff or flexible plastic material. Polyvinyl chloride plastic can be used for many different applications. As will be further discussed, other plastic materials may be used.

FIGS. 4–11 illustrate apparatus and steps in a preferred method which may be used in the manufacture of the catheter 10 according to the present invention.

Figure 5:
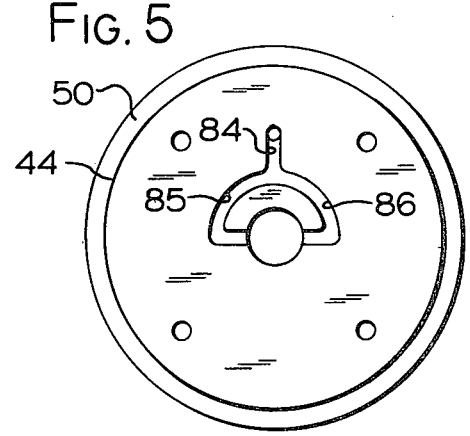
FIG. 5 is a bottom end view of a die member used in the die shown in FIGS. 4 and 6.

The extruding apparatus of FIGS. 4–6 includes an extruding die 32 having a cylindrical die body or housing 34 containing a die bushing 36, and a hollow die pin 38 extending within the bushing. The die pin 38 has a hollow mounting pin 40 connected in fixed relation with the extruded fixture (not shown) and to a conventional source of pressurized air indicated at 42. The bushing 36 includes upper and lower bushing members 44 and 46, respectively, which are connected together by a plurality bolts 48, and may be provided with cooperating dowel pins and dowel holes (not shown). In FIG. 5 four bolt holes for bolts 48 are shown. The upper member 44 has a flange 50 clamped between upper and lower housing members 42 and 54 respectively which are connected by bolts 56 to the extruder fixture. The die pin 38 has an upper cylindrical portion 58, a connical midportion 60, and a lower tubular or cylindrical portion 62 forming with the lower die member 46 a die outlet or orifice at 64. The bushing 36 and die pin 38 are in spaced relation to provide primary plastic flow channel 65 connected between the die orifice 64 and a primary plastic die inlet 68 which is connected, in turn, to a primary extruder 70. The die inlet 68 is shown also in FIG. 6.

Primary plastic 66 from which body 12 of catheter 10 of FIG. 1 is made, flows from the die orifice 64 in the form of molten plastic extrudate or tubing and forms the major portion of extrudate 72. The pressurized air flowing through the die pin 38 from source 42 insures that the molten tubing 72 has a lumen 74 of predetermined diameter.

In addition to the primary plastic material 66 from which the catheter 12 is formed, a groove forming second or auxiliary plastic material 76 from a second or auxiliary extruder 78 is employed in producing the extrudate 72. Molten auxiliary plastic material 76 flows from extruder 78, through a control valve 80 and into an auxiliary die inlet 82 in the upper die member 44. The auxiliary die inlet 82, as best seen in FIG. 6, connects with a downwardly or axially extending channel 83 which, in turn connects with a radially extending channel 84 in die member 44. The channel 84, as seen in FIG. 5, connects with a pair of generally arcuate channels 85 and 86 which extend circumferentially in opposite directions from channel 84 and terminate at and connect with the extrudate channel 65 respectively at diametrically opposite locations or at locations 180° apart. Channels 84, 85 and 86 are formed in the bottom-face of die memer 44, and the upper face of die member 46 closes these channels. The molten auxiliary plastic 76 flows from arcuate channels 85 and 86 and into the outer walls of the primary plastic extrudate 66 in channel 65 at a point between the cylindrical die pin portion 62 and the bushing 36.

The flow of auxiliary plastic 76 is automatically controlled by any suitable control system or programmer, such as programmer 87 in FIG. 4, which controls the operation of control valve 80 to cause a predetermined effective groove forming amount of auxiliary plastic 76' to be introduced into the outer opposite sides of the cylindrical portion of the stream of the primary plastic or molten tubular extrudate at predetermined time intervals or at predetermined spaced locations along the extrudate 72. The programmer is shown controlling the operation of both extruders 70 and 78, the pressurized air source 42 and control valve 80. The control valve 80 may include a conventional three-way valve which selectively and proportionally delivers plastic 76 to the die inlet 82 and a scrap barrel 88. Passing molten plastic into the scrap barrel 88 when the control valve 80 is not fully open prevents pressure build-up in the system. The flow rate of plastic to inlet 82 from the extruder 78 could of course be manually controlled by a manually controllable valve if desired.

Figure 7:
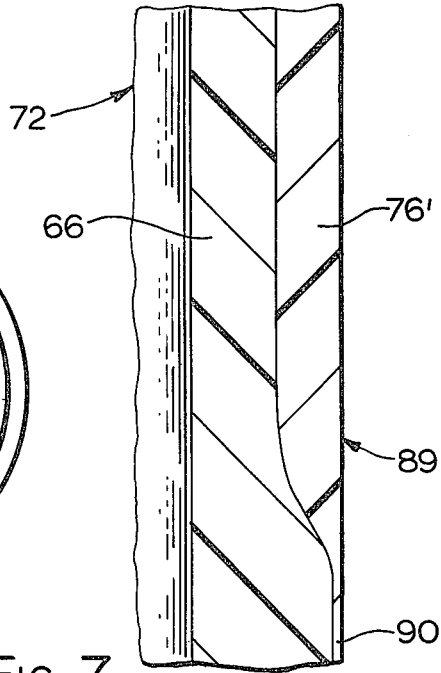
FIG. 7 is an enlarged fragmentary cross-sectional view of the sidewall of the extrudate from the die of FIG. 4.

The control valve 80 is controlled by programmer 87 during extrusion of primary plastic 66 such that an effective strip or segment 76', as seen in FIGS. 4, 7 and 8, of auxiliary plastic 76 of predetermined length is intermittently introduced into the exterior of the sidewall of extrudate 72 at selected intervals and on each of the opposite sides of the extrudate. FIG. 7 shows, on an enlarged scale, a portion of the extrudate 72 containing both plastics 66 and 76. Preferably, the control valve 80 is operated to continuously supply auxiliary plastic to die 32 in a manner to produce a continuous integral auxiliary plastic strip 89 which includes groove forming members or segments 76' and member-connecting strip elements or connectors 90 between the members 76'.

In FIG. 8, the extrudate 72 is shown rotated 90° about its longitudinal axis from its orientation in FIG. 4 in order to show one of the strips 89 with its several groove forming members 76' and connectors 90. The auxiliary plastic material 76 which forms the strips 89 is different from that of the primary plastic 66 such that the auxiliary plastic 76 will not bond to the plastic 66 under molten conditions or in die 32 so that the strips 89 are subsequently easily removed from the extrudate 72, for example, when the strip 89 solidifies such as when it is cooled. FIG. 9 shows one of the strips 89 removed from the extrudate 72. When the two strips 89 (one shown) are removed from the extrudate 72, plastic tubing 91 is provided which has corresponding axially extending grooves 92 in the exterior of the sidewall of the extrudate 72 where members 76' had been located. There are two grooves 92 on diametrically opposite sides of the tubing 91, however, more than two may be used. For example three or four equally circumferentially spaced grooves may be formed if desired.

The rate of flow of auxiliary plastic 76 may be such that the depth of the plastic 76' are approximately 30% to 50% of the average thickness of the sidewall of the extrudate (FIG. 7), while the thickness of the auxiliary plastic segment connectors 90 are made much less than that of the members 76'. The connectors 90 are preferably made very thin, for example, they may be one to three thousandths of an inch thick so that when removed from the extrudate 72, the outer surface of the extrudate or finished catheter is substantially not affected or such that there is little indication that the connectors 90 had been coextruded with the primary plastic 66. No marks or grooves are shown in the illustrated tubing 91 or in the finished catheter 10 as a result of the thin connectors 90, however, depending upon the thickness of the connectors 90, there may be a groove in the finished tubing which can be felt with the fingers. As long as such a groove is relatively shallow, it will not undesirably weaken the catheter or result in undesirable kinking of the catheter. The connectors 90, in most cases, are preferably made as thin as possible but not so thin that they break or do not generally result in a continuous or non-broken strip 89 during extrusion. The minimum thickness of connectors 90 will also depend upon the type of auxiliary plastic used.

By making the auxiliary plastic strip 89 continuous, its removal from the extrudate 72 during the continuous extrusion process is greatly facilitated. The strip 89 can be conveniently and efficiently pulled away from the extrudate 72 and wound onto a roller or the like during the extrusion of the extrudate. The plastic members 76' may be extruded without the connectors 90 although removal of members 76' may not be accomplished as readily in such a case.

The primary and auxiliary plastic materials 66 and 76 should be dissimilar enough that they do not bond to one another, as previously pointed out, and can be readily removed from the extrudate after it issues from the die orifice 64. These plastic materials also should have melt temperatures sufficiently close to allow both to be effectively coextruded. Good results have been obtained using polyvinyl chloride as the tube body 12 plastic and polyethylene as the auxiliary plastic 76. Other combinations of plastics are also usable in the process disclosed herein. For example, polypropylene may be used as the auxiliary plastic when the tube plastic is polyvinyl chloride. Also, where the tube plastic is polyurethane, the auxiliary plastic may be, for example, polyethylene or polypropylene. Thus, as long as the two plastic materials, primary and auxiliary, are coextrudable and can be separated from each other after coming from the extrusion die or when solidified, they are usable to provide a plastic tube having grooves.

After the auxiliary strip material 89 is removed from the solidified or partially solidified extrudate 72 to produce tubing 91, the tubing may be separated into tubes such as by cutting along lines 93 and 94 as seen in FIG. 10. A cut along line 93 does not intersect a groove 92 while a cut along line 94 would intersect a groove 92. Thus, a section of the tubing so cut would have a portion of two grooves 92 at one end while the other end would not have a groove. By cutting through the middle of groove 92 and also at a point midway between axially spaced grooves, substantially all of the extrudate can be economically employed in making catheters. Of course, tubes could be produced with grooves if formed by cutting through tubing 91 at locations other than at lines 93 and 94.

Another step in producing the catheter 10 of FIG. 1 is to insert the grooved end of a section of tubing cut along lines 93 and 94 into a mold or die 96, as seen in FIG. 11. Mold 96 has a cup or rounded shape. The die 96 is heated such that the tip end of the plastic tube melts and becomes rounded. During this heat forming step, the plastic material at the tip of the tube melts and flows into the lower ends of the grooves filling a distal end portion of the groove as seen at 98 in FIG. 1.

Before or after the tube end is heat formed to round the tip, the holes 30 may be punched or drilled into the bottom wall of each of the grooves 26 and 28. For example, where grooves 26 and 28 are formed diametrically on opposite sides of the tube as in the illustrated embodiment, a punch may efficiently and simply be passed through both sides of the catheter in a single stroke to form a hole on each of the opposite sides of the tube, that is in both grooves 26 and 28. While two holes are shown in each groove one or more may be formed.

While two recess grooves 26 and 28 are shown in the illustrated embodiment, a different number of such grooves may be used where desired as previously mentioned. In such case, one or more suction holes may be formed in the bottom wall of each such groove.

The severed end adjacent the groove may be heat formed to round the end whether or not the tubing 91 is severed through a groove 92. Also, this heat forming of the end as in FIG. 11 does not increase the outer diameter of the tube or reduce the inner diameter of the tube. Even though the tubing 91 is economically cut across a groove 92 in FIG. 10, the leading edge of groove is rounded in the die 96 (FIG. 11) so that the distal end 22 (FIG. 2) is smooth and rounded to prevent damage to the cavity walls when inserted.

In FIG. 12, the catheter 10 is shown connected to a source of vacuum or suction source 100 through a conventional vacuum regulating or control member 102. The control member is frictionally connected or otherwise fixed to the proximal end of catheter 10. Member 102 includes a vent port 104 which may be manually opened (or partially opened) or closed to make or break the negative pressure at the distal end of the catheter. A control member similar to member 102 is disclosed in U.S. Pat. No. 3,885,565. Instead of connecting a separate vacuum control member such as member 104 to the catheter, the catheter may be provided with an opening in the sidewall at the proximal end which can be manually opened and closed to control the negative pressure at the distal end. For example, U.S. Pat. Nos. 3,848,604 and 3,945,385 disclose catheters having an integral bubble formed in the catheter body during the extrusion process and which is provided with a controllable vent hole. Such an integral bubble can have a tube connector end to be used to readily connect the catheter to a vacuum line or tube.

As various changes could be made in the above construction and method of making or process for making the catheter without departing from the scope of the invention, it is intend that all matter contained in the above description and apparatus shown in the accompanying drawings shall be interpreted as illstrative and not in a limiting sense.

I claim:

1. A method of making plastic tubing having a selected wall portion thereof with a wall thickness less than that of wall portions adjacent thereto and an opening through that wall portion comprising the steps of coextruding first and second plastic materials so as to form plastic tubing of the first plastic material with the second plastic material in the sidewall of the tubing, the first and second plastic materials being capable of separation after solidification, removing the second plastic material from the tubing to provide tubing having a wall portion of less thickness than wall portions adjacent thereto, and forming an opening through that wall portion.

2. A method of making plastic tubing having a groove and an opening extending through the bottom wall of the groove comprising the steps of extruding a first plastic material to produce a molten tubular extrudate, while extruding the tubular extrudate extruding a second molten plastic material including the step of extruding the second plastic material at a location in the exterior of the sidewall of the molten tubular extrudate, the first and second plastic materials being capable of separation after extrusion, allowing the second plastic material to solidify, removing the solidified second plastic material from the sidewall of the tubular extrudate to provide tubing with a groove where the second plastic material was removed and forming an opening through the bottom wall of the groove.

3. The method of claim 2 wherein said step of extruding a second molten plastic material includes also extruding the second plastic material in the exterior of the sidewall of the molten tubular extrudate at a second location circumferentially spaced from the first named location, allowing the second material at the second location to solidify and removing it from the second location to provide said tubing with a groove circumferentially spaced from the first named groove, and forming an opening through the bottom wall of the second groove.

4. The method of claim 2 wherein the first plastic material is extruded so that the tubular extrudate has substantially constant inner and outer diameters throughout a major portion of the length thereof.

5. The method of claim 2 wherein the first plastic material includes polyvinyl chloride and the second plastic material includes a different plastic.

6. The method of claim 5 wherein the different plastic includes polyethylene.

7. A method of making plastic tubes having a groove and an opening extending through the bottom wall of the groove comprising the steps of extruding a first plastic material to produce a molten tubular extrudate, while extruding the tubular extrudate extruding a second plastic material including the step of extruding the second plastic material at a location in the exterior of the sidewall of the molten tubular extrudate during selected time intervals to produce axially spaced groove forming plastic strips in the extrudate, the first and second plastic materials being capable of separation after extrusion, allowing the second plastic material to solidify, removing the solidifed second plastic material from the sidewall of the tubular extrudate to produce a groove where each plastic strip was removed, separating the extrudate into tubes so that each tube includes a groove formed by at least a portion of one of the grooves in the extrudate, and forming an opening through the bottom wall of each groove so that each tube has a groove with an opening therein.

8. The method of claim 7 wherein said step of extruding a second molten plastic includes extruding the second plastic material between the plastic strips to form connecting plastic elements integrally interconnecting adjacent ends of successive plastic strips, the second plastic being extruded such that the connecting elements are substantially thinner than the plastic strips.

9. The method of claim 8 wherein the plastic connecting elements are less than about three one-thousandts of an inch.

10. The method of claim 7 or 8 wherein said step of extruding a second molten plastic material includes extruding the second plastic material also in the exterior of the sidewall of the molten tubular extrudate during said selected time intervals but at a location circumferentially spaced from the first named location to produce other axially spaced groove forming strips in the extrudate circumferentially spaced from the first named strips and provide other axially spaced grooves when the solidified second plastic material is removed from the sidewall of the tubular extrudate, and forming an opening through the bottom wall of each of the other grooves.

11. The method of claim 10 wherein said step of extruding a second molten plastic includes extruding the second plastic material between said other plastic strips to form other connecting plastic elements integrally interconnecting adjacent ends of other plastic strips, the second plastic material being extruded such that the other connecting elements are substantially thinner than the other plastic strips.

12. The method of claim 11 wherein said other plastic connecting elements are less than about three one-thousandths of an inch.

13. The method of claim 7 wherein said first plastic material includes polyvinyl chloride and said second plastic material includes a plastic other than polyvinyl chloride and which is removable from the tubular extrudate when both of said plastic materials are solidifed.

14. The method of making plastic suction catheters comprising the steps of extruding a first plastic material to produce molten tubular extrudate, extruding a second plastic material while extruding the molten tubular extrudate including the step of extruding the second plastic material at a location in the exterior of the sidewall of the molten tubular extrudate during selected time intervals to produce a plurality of successively extruded groove forming plastic members at axially spaced positions in the sidewall of the extrudate, the first and second plastic materials being different and capable of separation after solidication thereof, allowing the second plastic material of said members to solidify, removing the solidified members from the tubular extrudate to provide axially spaced grooves in the tubular extrudate where the plastic members were removed, separating the extrudate into tubes of predetermined length so that each tube includes a groove formed by at least a portion of one of the grooves of the tubular extrudate, and forming a suction opening through the bottom wall of each of the grooves so that each tube has a suction opening and can serve as a suction catheter.

15. The method of claim 14 wherein said step of extruding a second molten plastic material includes extruding the second plastic material also in the exterior of the sidewall of the molten tubular extrudate during said selected time intervals but at a location circumferentially spaced from the first named location to produce a second plurality of axially spaced groove forming plastic members in the extrudate circumferentially spaced from the first named plastic members, allowing the plastic members of said second plurality of plastic members to solidify, removing the second plurality of plastic members from the extrudate to provide a second plurality of grooves circumferentially spaced from the first named plurality of grooves, and forming a suction opening through the bottom wall of each groove of the second plurality of grooves, whereby each of said tubes separated from the extrudate also includes a groove and a suction opening circumferentially spaced from the first named suction opening and groove of each tube.

16. The method of claim 14 wherein said step of extruding a second plastic material includes extruding the second plastic material continuously at both of said circumferentially spaced locations during and between said time intervals to produce first and second strips of the second plastic material with the first strip including said first named plastic members and integral plastic elements interconnecting adjacent ends of said first named plastic members and with the second strip including said second plurality of plastic members and a second plurality of connecting elements integrally connecting adjacent ends of successive plastic members of said second plurality of members and such that said first named and second pluralities of elements are substantially thinner than said plastic members of said first named and second pluralities of members, allowing both of said strips to solidify and removing both of said strips from the extrudate.

17. The method of claim 14 or 16 wherein the step of separating the extrudate into tubes includes severing the extrudate through a groove so that each tube has a groove extending to the end thereof, and heat forming said end of each tube to smooth that end and cause plastic material of the tube to flow into an end portion of the groove of the tube.

18. The method of claim 16 wherein said first and second strips are peeled from the extrudate during extrusion thereof.

19. The method of claim 18 wherein said first and second strips are wound on a mandrel during extrusion of the tubular extrudate.

20. The method of claim 16 wherein each of said plastic members is extruded so that it has a depth of between about 30% and 50% of the sidewall thickness of the tube and the depth of each of said elements is less than about 3/1000 of an inch.

21. The method of claim 14 or 16 wherein said first plastic material includes polyvinyl chloride.

22. The method of claim 21 wherein said second plastic material is polyethylene.

23. The method of claim 15 or 16 wherein said first plastic material is extruded through a tube forming die to produce the tubular extrudate, and wherein said second plastic is extruded through a pair of channels in the die which introduce the second plastic material into the tubular extrudate at the circumferentially spaced locations.

24. The method of claim 23 wherein said circumferentially spaced locations are about 180° apart.

25. The method of claim 24 wherein each tube is formed with grooves located 180° apart and wherein the holes formed in these grooves are formed by moving a punch through both grooves on a single stroke of the punch.

26. A suction catheter made in accordance with the method of claim 14, 15 or 16.

* * * * *